US00PP21197P2

(12) United States Plant Patent
Giesen

(10) Patent No.: US PP21,197 P2
(45) Date of Patent: Aug. 10, 2010

(54) ***SUTERA* PLANT NAMED 'CAY JUWIT09'**

(50) Latin Name: *Sutera cordata*
Varietal Denomination: Cay Juwit09

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/383,789

(22) Filed: Mar. 27, 2009

(51) Int. Cl.
*A01H 5/00* (2006.01)

(52) U.S. Cl. ..... Plt./485

(58) Field of Classification Search ..... Plt./485
See application file for complete search history.

*Primary Examiner*—June Hwu
(74) *Attorney, Agent, or Firm*—S. Matthew Edwards

(57) ABSTRACT

A new *Sutera* plant named 'Cay Juwit09' particularly distinguished by large, white flowers, medium green foliage, medium to large sized, dentate leaves, fair branching and bushy, low mounding to trailing plant habit, initially compact, later developing to about medium size.

1 Drawing Sheet

Latin name of the genus and species of the plant claimed: *Sutera cordata.*

Varietal denomination: 'Cay Juwit09'.

BACKGROUND OF THE NEW PLANT

The present invention comprises a new and distinct cultivar of *Sutera*, botanically known as *Sutera cordata* and hereinafter referred to by the cultivar name 'Cay Juwit09'.

'Cay Juwit09' is a product of a planned breeding program. The new cultivar originated from a hybridization made in July 2005 in Andijk, Netherlands.

The female parent was an unpatented, proprietary *Sutera* plant designated 'BA05-93-1'. 'BA05-93-1' has smaller white flowers and shorter stems than 'Cay Juwit09'.

The male parent of 'Cay Juwit09' was an unpatented, proprietary *Sutera* plant designated 'BA04-10-1' having a white flower color. 'BA04-10-1' has a less deep green foliage color and more compact plant habit than 'Cay Juwit09'.

The resulting seeds were sown in October 2005, and 'Cay Juwit09' was selected as one flowering plant within the progeny of the stated cross in January 2006 in a controlled environment in Andijk, Netherlands.

The first act of asexual reproduction of 'Cay Juwit09' was accomplished when vegetative cuttings were taken from the initial selection in the spring of 2006 in a controlled environment in Andijk, Netherlands.

Horticultural examination of plants grown from cuttings of the plant initiated in the spring of 2006 in Andijk, Netherlands, and continuing thereafter, has demonstrated that the combination of characteristics as herein disclosed for 'Cay Juwit09' are firmly fixed and are retained through successive generations of asexual reproduction.

'Cay Juwit09' has not been observed under all possible environmental conditions. The phenotype may vary significantly with variations in environment such as temperature, light intensity and day length.

Plant Breeders' Rights for this cultivar were applied for with the European Union on Jul. 21, 2008. 'Cay Juwit09' has not been made publicly available more than one year prior to the filing of this application.

DESCRIPTION OF DRAWING

This new *Sutera* plant is illustrated by the accompanying photograph which shows blooms, buds, and foliage of the plant in full color. The colors shown are as true as can be reasonably obtained by conventional photographic procedures. The photograph is a view of foliage canopy with shoot tips, buds and flowers, while the inset shows a close-up of the flowers.

DETAILED BOTANICAL DESCRIPTION

The measurements were taken in Hillscheid, Germany, in mid June 2008 on 17-18 week old plants that were growing, 3 each, in 25 cm diameter baskets in a greenhouse at relatively cool conditions. Culture of these plants had started in early February 2008 with planting of rooted cuttings that had been pinched once.

Color chart used: The Royal Horticultural Society Colour Chart (R.H.S.), 2001.

BRIEF SUMMARY OF THE INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Sutera* as a new and distinct variety:

1. Large, pure white flowers.
2. Medium green foliage with medium to large, dentate leaves.
3. Bushy, low mounding to trailing plant habit.
4. Grows with about medium vigor.
5. Initially compact, later about medium sized plants.

COMPARISON WITH COMMERCIAL CULTIVARS

'Cay Juwit09' differs from the commercial Sutera cultivar, 'Taifun white,' protected as 'Wesbawei' (U.S. Plant Pat. No. 14,444) in that 'Cay Juwit09' has larger flowers and larger leaves than 'Wesbawei.' Additionally, 'Cay Juwit09' develops fewer but thicker branches.

'Cay Juwit09' differs from the commercial cultivar 'Dancop 25' (U.S. Plant Pat. 19,747) by having a more compact plant habit with distinctly shorter branches.

Plant:

*Growth and habit.*—Medium vigor, initially compact, fair branching with relatively thick stems, initially spreading, later low mounding to trailing, moderately tight.

*Height.*—15-20 cm (above soil).

*Width* (*diameter*).—30-40 cm, including flowers.

*Number of branches.*—15-20.

*Time to produce a finished flowering plant.*—About 12-13 weeks for a 12 cm pot.

*Outdoor plant performance.*—Used for hanging baskets or in mixed container plantings.

*Time to initiate and develop roots.*—21 days at 20-24° C.

*Root description.*—Fine, fibrous and freely branching.

Stem:

*Characteristics.*—Cross section round, fair degree of self-branching.

*Stem length.*—13-18 cm.

*Diameter.*—3 mm.

*Internode length.*—1.3-2.0 cm.

*Color.*—RHS 138A, no anthocyanin.

*Texture.*—Pubescent.

Foliage:

*Arrangement.*—Alternate.

*Leaf shape.*—Initially deltoid, later nearly round.

*Apex.*—Acute.

*Base.*—Initially truncate, later cuneate.

*Margin.*—Dentate.

*Leaf length.*—Up to 1.5 cm.

*Leaf width.*—Up to 1.4 cm.

*Immature leaf, color upper surface.*—RHS 137D to 138A.

*Immature leaf, color lower surface.*—RHS 138A to 138B.

*Mature color upper surface.*—RHS 137A.

*Mature color lower surface.*—RHS 137D.

*Venation type.*—Pinnate.

*Venation color.*—RHS 143C.

*Texture.*—Both surfaces covered with short, dense pubescence.

Petiole:

*Length.*—0.3 cm.

*Petiole width.*—1 mm.

*Petiole color.*—RHS 143C.

*Texture.*—Pubescent.

Inflorescence:

*Blooming habit.*—Continuous through the growing season from spring to the fall.

*Type of inflorescence.*—Solitary, flowers emerge from the leaf axils of the upper stem nodes, usually 2 flowers per node.

*Quantity of flowers per stem.*—About 3-6 flowers and additional buds in a cluster at the end of the stem.

*Fragrance.*—None.

Pedicel:

*Color.*—RHS 143B.

*Length.*—0.2-0.4 cm.

*Diameter.*—0.1 cm.

*Texture.*—Dense pubescence.

Flower:

*Corolla type and shape.*—Single-type, nearly round, lower part funnel-shaped formed by 5, mainly fused petals, upper part is salver-shaped formed by the partly free petal lobes.

*Corolla diameter.*—2.3-2.5 cm.

*Corolla tube length.*—0.7-0.8 cm.

*Flower length.*—About 1.2 cm.

*Funnel diameter.*—0.4-0.5 cm.

*Color upper surface.*—Pure white, whiter than RHS 155D.

*Color lower surface.*—RHS 155D.

*Color of throat.*—Deep yellow, RHS 21A.

*Color of funnel outer side.*—RHS 21B to 21C.

Petal (lobes):

*Apex.*—Rounded.

*Base.*—Fused.

*Margin.*—Entire.

*Texture.*—Upper side glabrous, under side with very short pubescence, increasing towards the funnel opening.

*Length of lobes*, (*from the corolla opening*).—6-7 mm.

*Width of lobes.*—8-9 mm.

Flower bud:

*Shape.*—Cone-shaped.

*Diameter.*—0.5-0.6 cm.

*Length.*—1.0-1-2 cm.

*Color* (*at tight bud*).—Greenish-white, RHS 150D.

Calyx:

*Shape.*—5 sepals in a whorl around the flower base.

*Sepal shape.*—Lanceolate, fused at the base.

*Sepal color.*—RHS 137C-137D.

*Length.*—0.7-0.9 cm.

*Width.*—About 1 mm.

*Apex.*—Acuminate.

*Base.*—Fused.

*Texture, upper surface.*—Glabrous.

*Texture, lower surface.*—Covered in dense hairs.

Reproductive organs stamens:

*Quantity.*—4.

*Filament, color.*—White, RHS 155D.

*Length.*—1.5-1.6 cm.

*Diameter.*—0.1 cm.

*Anther color.*—Yellow, RHS 12B.

*Pollen amount.*—Moderate.

*Pollen color.*—Yellow, RHS 12A.

Pistil:

*Quantity per flower.*—One.

*Length.*—1.1-1.3 cm.

*Stigma color.*—Light green, RHS 144A.

*Style color.*—Greenish white, RHS 145C.

Fruit and seed set: Has not been observed.

Disease and insect resistance: Resistance and susceptibility typical for the species, no special observations made.

What is claimed is:

1. A new and distinct cultivar of *Sutera* plant named 'Cay Juwit09' plant substantially as illustrated and described herein.

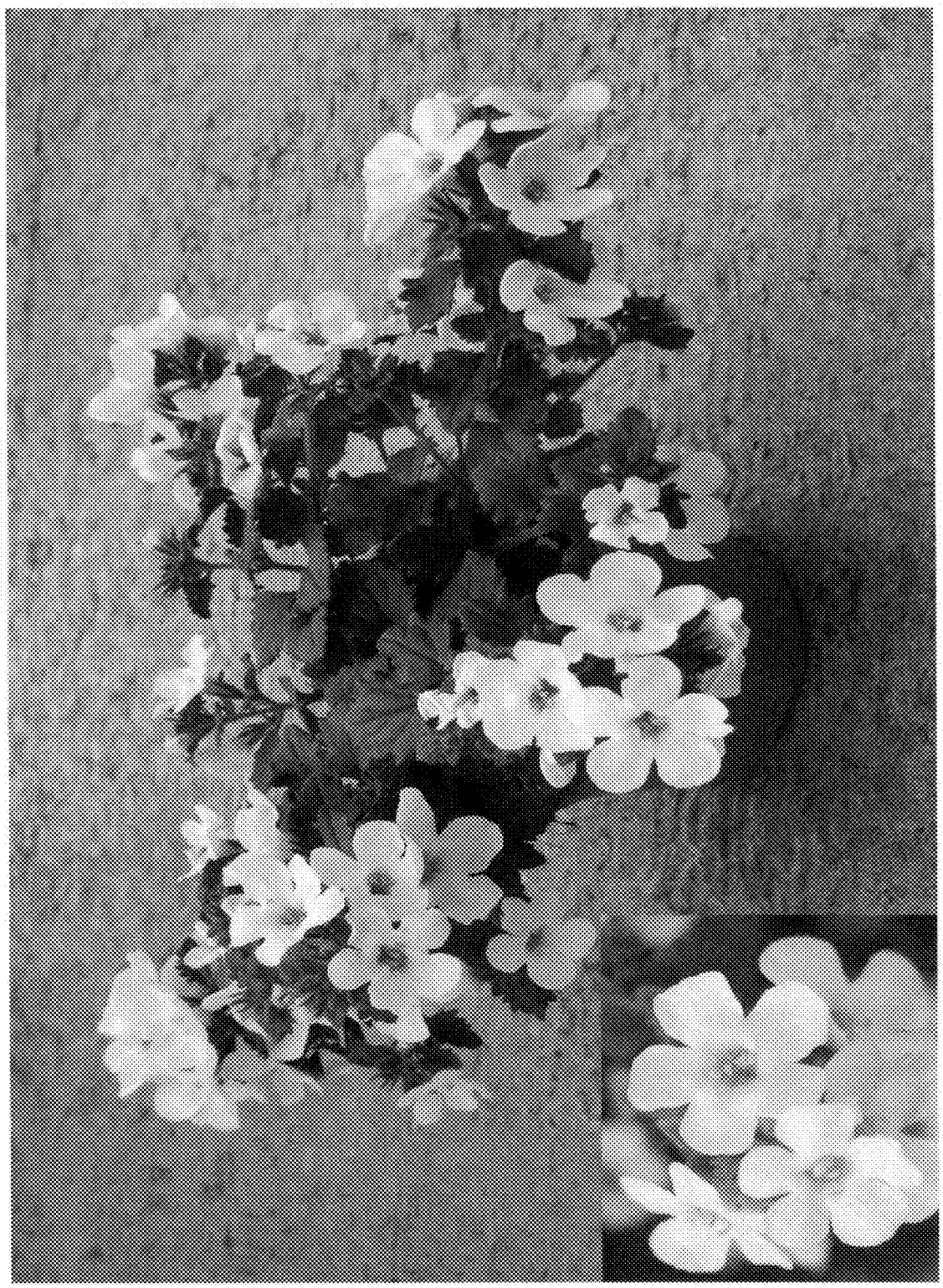

* * * * *